US011683690B2

(12) United States Patent
Obaidi

(10) Patent No.: US 11,683,690 B2
(45) Date of Patent: Jun. 20, 2023

(54) METHODS AND SYSTEMS FOR SECURE OPERATION OF IMPLANTABLE DEVICES

(71) Applicant: T-Mobile USA, Inc., Bellevue, WA (US)

(72) Inventor: Ahmad Arash Obaidi, Issaquah, WA (US)

(73) Assignee: T-Mobile USA, Inc., Bellevue, WA (US)

( * ) Notice: Subject to any disclaimer, the term of this patent is extended or adjusted under 35 U.S.C. 154(b) by 697 days.

(21) Appl. No.: 16/358,540

(22) Filed: Mar. 19, 2019

(65) Prior Publication Data

US 2020/0305000 A1 Sep. 24, 2020

(51) Int. Cl.
| | |
|---|---|
| *H04W 12/088* | (2021.01) |
| *G06F 16/22* | (2019.01) |
| *G16H 40/67* | (2018.01) |
| *A61N 1/372* | (2006.01) |
| *A61F 2/02* | (2006.01) |
| *A61F 2/14* | (2006.01) |
| *A61F 2/38* | (2006.01) |
| *A61M 5/142* | (2006.01) |
| *G06F 21/57* | (2013.01) |

(Continued)

(52) U.S. Cl.
CPC ........... *H04W 12/088* (2021.01); *A61F 2/022* (2013.01); *A61F 2/14* (2013.01); *A61F 2/38* (2013.01); *A61M 5/14276* (2013.01); *A61N 1/37254* (2017.08); *G06F 16/22* (2019.01); *G06F 21/575* (2013.01); *G16H 40/67* (2018.01); *H04W 12/50* (2021.01); *A61B 5/14532* (2013.01); *A61F 2002/183* (2013.01); *A61F 2002/3067* (2013.01); *A61F 2250/0002* (2013.01); *A61M 2205/3523* (2013.01); *A61N 1/36046* (2013.01); *A61N 1/3956* (2013.01); *G06F 2221/034* (2013.01)

(58) Field of Classification Search
CPC .... H04W 12/088; H04W 12/50; G16H 40/67; A61N 1/37254; A61N 1/3956; A61M 5/14276; G06F 21/575; G06F 21/554; G06F 21/606; A61F 2/02; A61F 2/482; A61F 2002/30668; H04L 67/12; A61B 5/0031

See application file for complete search history.

(56) References Cited

U.S. PATENT DOCUMENTS

| | | | | |
|---|---|---|---|---|
| 2006/0031378 | A1* | 2/2006 | Vallapureddy | G16H 40/63 600/300 |
| 2010/0292556 | A1* | 11/2010 | Golden | G06Q 10/06 607/31 |
| 2016/0317822 | A1* | 11/2016 | Rao | A61N 1/37 |

\* cited by examiner

*Primary Examiner* — Shewaye Gelagay
*Assistant Examiner* — Carlton Johnson
(74) *Attorney, Agent, or Firm* — Lee & Hayes, P.C.

(57) ABSTRACT

Implantable devices, such as artificial organs, increasingly incorporate hardware, software, firmware, and/or wireless communication capabilities. For example, such implantable devices can utilize wireless technology to allow for efficient configuration, maintenance, and operational analysis. As these implantable devices become more connected, electronic security will become more important. This disclosure relates to implantable devices that may utilize a secure boot process and secure communication, both between artificial devices in the human body and between these devices and the external world. This disclosure provides secure communication approaches for maintaining the digital privacy and integrity of artificial devices, for protecting the individual from malicious hacking of data, and for controlling of such implantable devices.

19 Claims, 7 Drawing Sheets

(51) Int. Cl.
*H04W 12/50* (2021.01)
*A61B 5/145* (2006.01)
*A61N 1/36* (2006.01)
*A61F 2/18* (2006.01)
*A61F 2/30* (2006.01)
*A61N 1/39* (2006.01)

METHODS AND SYSTEMS FOR SECURE OPERATION OF IMPLANTABLE DEVICES

BACKGROUND

Devices and systems implanted in patients can monitor body conditions, treat medical conditions, as well as enhance body functions. Example implantable devices include artificial hearts, pacemakers, implantable cardioverter defibrillator, insulin pumps, artificial kidneys, and cochlear implants. In addition, artificial joints and other prosthetic devices such as artificial knees, wrists, arms, and legs enhance mobility and other body functions. Biomedical devices increasingly typically rely on digital technology to enhance the functionality, reliability, and accuracy of these devices. However, incorporation of digital technology has also permitted the growth and exploitation of malicious digital functionality. For example, digital data generated, monitored, and stored by implantable devices may become a target of eavesdropping or nefarious modification.

Unauthorized receipt or use of digital data from implantable devices creates a multitude of issues. Viewing or capturing digital data may violate the privacy of the digital health data of a patient. Malicious hacking or authorized use of implantable devices may create safety issues. Malicious use of data and introduction of malicious software may change the operation and reliability of implantable devices, compromising patient safety. As implantable biomedical devices become more prevalent, powerful, and interconnected, cybersecurity issues should be addressed to minimize the risks of malicious activity affecting the integrity of operation of implantable devices.

BRIEF DESCRIPTION OF THE DRAWINGS

The detailed description is described with reference to the accompanying figures. In the figures, the left-most digit(s) of a reference number identifies the figure in which the reference number first appears. The same reference numbers in different figures indicate similar or identical items.

DETAILED DESCRIPTION

Figure 1:
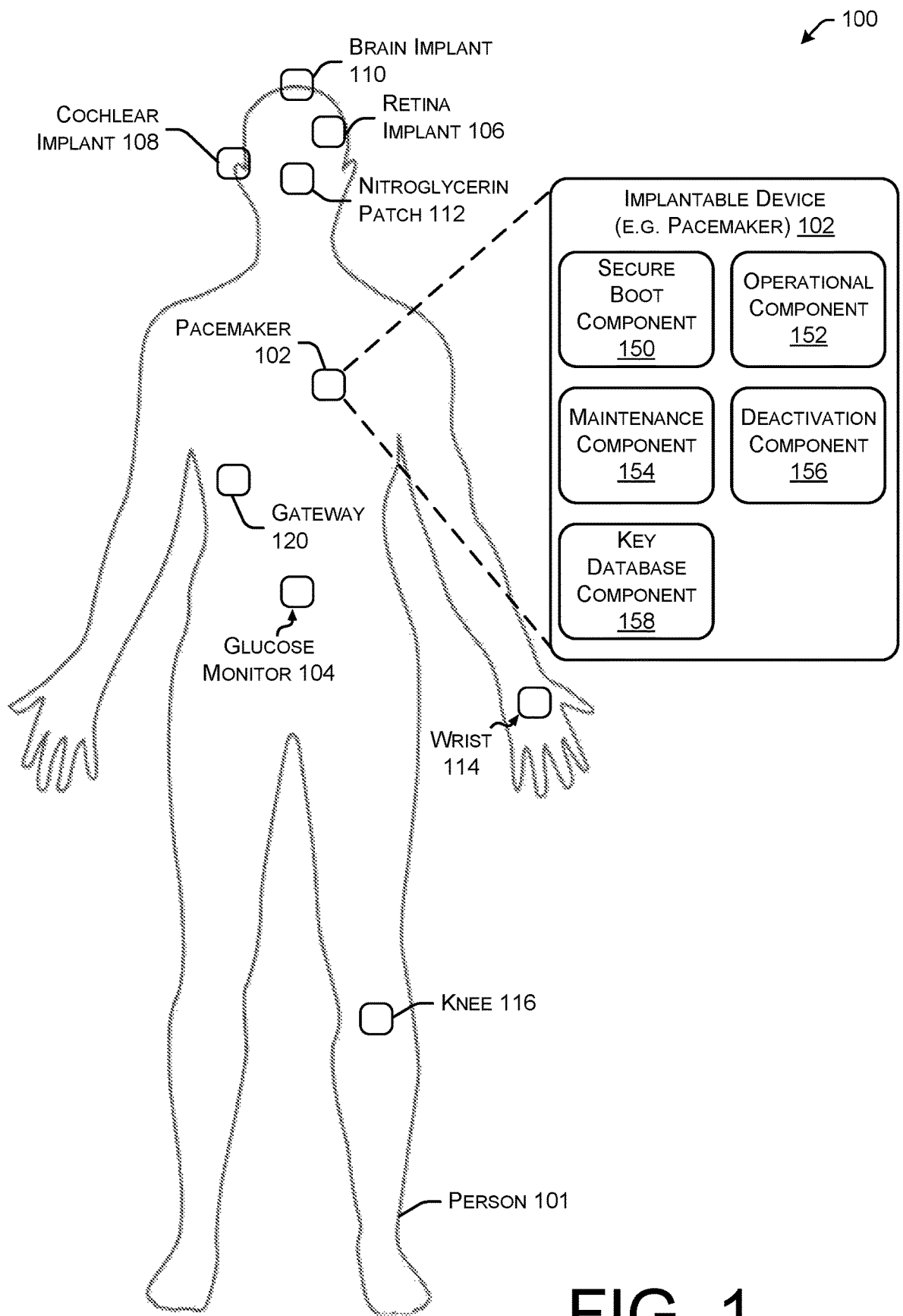
FIG. 1 is an illustrative environment for securing devices implanted in human organ systems.

This disclosure includes systems and methods for enhancing electronic security of implantable devices. Implantable devices such as artificial organs are often implanted to replace or supplement operation of tissue, organs, joints, etc., of a person. Implantable devices increasingly rely on digital technology, which presents unique challenges associated with start-up or boot procedures, maintenance (e.g., of software or firmware), and secure communication, processing, accessing, and storing of data. This disclosure provides systems and methods for enhancing electronic security of these digital implantable devices. Additionally, the systems and methods may minimize unauthorized devices, entities, or users from accessing the digital data and controlling or modifying the operation of the implantable devices.

Implantable artificial organs can use wireless communication for device configuration, maintenance, and organ function. As these devices become more connected, electronic security issues become critical for proper operation of these devices, and well as preventing the unauthorized use of the implantable device as a gateway to other devices and systems. As disclosed herein, implantable devices may utilize a secure boot process and secure communication channels for implantable devices, as well between implantable devices and devices in the external world. The disclosed systems and methods provide secure communication channels between implantable devices, maintain digital privacy and integrity of artificial devices, maintain digital security, and protect from malicious hacking or malicious use of the data, protect from malicious control of these artificial organs, and may prevent network intrusions.

The disclosed systems and methods describe various embodiments of preventing malicious operation of implantable devices. For example, pacemakers may be programmed using induction or wireless technology, without any handshaking or authentication technology to prevent malicious operation or use. The disclosed systems and methods may provide secure communication pathways so that pacemakers and other implantable devices are less susceptible to malicious intrusion. By providing secure communication pathways, a protocol is presented for secure and authenticated communication across the ecosystem of implantable devices.

The disclosure is further directed toward securing the integrity of devices, implanted as part of human organ systems, from unauthorized electronic intrusions. Example organ systems include artificial cardiac systems, including artificial hearts and implantable pacemakers, implantable cardioverter defibrillators, and artificial pancreas systems. Implantable devices are increasingly controlled by digital processing devices, which allows for automatic control and monitoring of these implantable devices, but also comes with risk. For example, digital processing devices can be susceptible to data intrusions and malicious hacking of the implantable device, and potentially devices and systems coupled to the implantable device, each of which may be detrimental. The disclosure describes systems and methods for facilitating a secure boot of an implantable device and for facilitating secure communications with the implantable device, thereby minimizing the risk of a malicious control of implantable devices.

The disclosed methods and systems can provide additional layers of data security and communication. In one example, a secure peer-to-peer communication between implantable devices is disclosed. In various examples, techniques for implementing secure communications with authorized devices and preventing communication with unauthorized devices are described.

In some instances, prior to commencing operation, an implantable device can be powered up and initialized by a secure boot process. The secure boot process can ensure that the device is operating properly under an authorized request. The secure boot process can ensure that the implantable device operates properly and should not fail during future operation. Following a secure boot, a secure communication pathway may be established with the implantable device. The secure communication pathway can enhance the integrity and security of data exchange with the implantable device. A secure communication pathway can maintain privacy by preventing unauthorized eavesdropping on the data communicated with the implantable device. Ensuring data integrity may reduce the risk of aberrant data, which may cause improper operation. A secure communication pathway may reduce the possibility of an unauthorized entity or device controlling or affecting the implantable device. A secure communication pathway may also reduce the possibility of an unauthorized party introducing malicious code that may affect the operation of the implantable device or devices coupled thereto. In one example, secure communication provides a communication pathway for secure monitoring of parameters such as pacemaker battery levels, insulin levels, and heart rhythm properties.

In some examples, a system for enhancing the cybersecurity of implantable devices includes a control component coupled to the implantable device. The control component includes a processor that, when executing computer instructions (e.g., stored in at least one memory), executes a secure boot process of the implantable device and establishes a secure communication pathway between the implantable device and an authorized device. The secure communication pathway prevents or reduces the risk of an unauthorized device accessing the secure communication pathway or the implantable device. In one example, the secure communication pathway is established as a wireless communication channel. Example wireless communication channels may include Wi-Fi (including 802.11-based technologies), cellular data service (including GSM, CDMA, CPRS, 4G, W-CDWM, EDGE, CDMA2000, LTE), WiMAX, Bluetooth, Zigbee (e.g., 802.15.4-based technologies), near field communication, frequency hopping, and the like.

The implantable device may perform various functions. In one example, an implantable device is programmed to perform one or more of the following operations: on-boarding or initializing an implantable device in a person or subject, operating the implantable device, maintaining the implantable device, servicing the implantable device, deactivating the implantable device, and reactivating the implantable device. The disclosed methods and systems permit the initiation of the operation of implantable devices in a body by on-boarding an implantable device in a body. On-boarding may include the physical operation associated with implanting the device and the initiation of the operation of the device. For example, when an implantable device is inserted in the body, the device may perform a self-check routine to establish the operation of the device and to identify errors or other abnormal conditions. The initiation phase may include booting the implantable device, thereby allowing software components to control the hardware of the implantable device.

After on-boarding and initiation of operation, the implantable device begins a normal operating phase. The normal operating phase includes normal and expected operation of the implantable device. Normal operation in the case of a pacemaker may include, for example, electrical pacing of the heart, when necessary, and recording the heart rhythm.

In addition to normal operation, the implantable device includes a maintenance component, which seeks to ensure proper and accurate operation of the implantable device during normal operation. Functions performed by the maintenance component may include self-diagnostic operations of the implantable device, the installation of software updates or upgrades, and software to resolve errors or potential errors. For example, a memory optimization routine may execute to ensure that memory is being used efficiently, including the removal of bad memory blocks and the optimization of memory storage allowing the device to operate more efficiently.

An implantable device may be decommissioned or deactivated. For example, an implantable device may be deactivated when a patient is undergoing surgery or another medical procedure that may be compromised by the implantable device. An implantable device may be deactivated upon determining that the implantable device's operation is harming or not otherwise helping the patient and should be removed from service. An implantable device may be deactivated by removing it from the body, inactivating it, or supplanting it by another device.

In some examples, a method for performing a secure boot process for an implantable device comprises providing power to the implantable device, obtaining a key unique to the implantable device, confirming the key unique to the implantable device, booting the implantable device, establishing a secure communication pathway, and communicating securing over the secure communication pathway. A key may be unique to an authorized user or to an implantable device. The implantable device may maintain a database or list of acceptable or authorized keys. In another example, information regarding the authorized unique keys may be stored on a device separate from the implantable device and may be accessible by the implantable device. During the secure boot process, the key is compared to the acceptable or authorized keys as a gating function to completion of the secure boot process. Confirmation of the unique key of the implantable device may facilitate the security of the boot process. In one example, the controller of the implantable device confirms whether the unique key is authorized, and if authorized, the secure boot process may be executed.

As used herein, the term "key" can refer to data from a source, wherein the data can indicate whether the source is an authorized party. In particular instances, a key can be a string of alphanumeric characters. In some implementations, a key can be in a payload of a data packet that is wirelessly transmitted from a particular source. In some examples, a key can be data packaged in a physical signal, such as at least one of a magnetic signal (e.g., a particular magnetic field), an electric signal, an ultrasonic signal, an electromagnetic signal (e.g., an infrared signal), or the like. In some implementations, a key can be compared to one or more authorized keys. When a key from a source matches one or more authorized keys, the source may be considered authorized. In some cases, the one or more authorized keys are stored in a local database.

As used herein, the term "handshake," and its equivalents, can refer to a process by which a first party and a second party establish a communication channel by exchanging one or more messages. In some cases, a handshake can include (i) transmitting, by the first party, a key to the second party, (ii) receiving, by the second party, the first key, and (iii) determining, by the second party, whether the key is an authorized key. In some cases in which the key is determined to be the authorized key, the handshake may include (iv) establishing, by the first party and the second party, a communication channel between the first party and the second party. In some cases in which the key is determined to be unauthorized (e.g., the key is determined to not be the authorized key), the handshake may include (v) blocking (or ignoring), by the second party, communication from the first party.

In an example, the secure communication pathway may be established between the implantable device and a gateway. A gateway may be a device wirelessly connected with the implantable device and serving as a communication node between the implantable device and external devices. In this example, the communication pathway may be implemented as a wireless communication channel between the implantable device and the gateway. In an example, the gateway operates as an access point to a network. In some instances, a secure communication pathway is established between authorized devices and the gateway creating a secure communication pathway between devices. Authorized devices may include implantable devices and external devices. In some instances, the gateway monitors communication between devices. In another example, the secure communication pathway may be established between the implantable device and an external device. For example, each external device may have a separate communication pathway with the implantable device. In another example, the secure communication channel may be established between the implantable device and the gateway and one or more external devices. A communication channel may be established between the gateway and the implantable device and between the gateway and numerous external devices. In addition, one or more external devices may have a direct communication channel, such as a wireless communication link, with the implantable device.

In an example, a method for operating an implantable device includes securely booting an implantable device and communicating securely with the implantable device via a secure communication pathway. Securely booting the implantable device may ensure that the implantable device is operating correctly and not being controlled by an unauthorized device or source. After a secure boot operation, the implantable device may establish a secure communication pathway preventing an unauthorized device (and unauthorized users) from accessing the secure communication pathway.

In various implementations, data can be exchanged between an implantable device and an authorized device over a secure communication pathway. In some cases, data indicating a condition of the implantable device can be transmitted to the authorized device over the secure communication pathway. For instance, if there is a software or hardware problem detected at the implantable device, data indicating the problem can be transmitted to the authorized device. In some cases, data indicating a sensed condition of an individual (e.g., a heart rhythm, an insulin level, a blood pressure, any other condition sensed by sensor(s) associated with the implantable device, etc.) in which the implantable device is implanted can be transmitted to the authorized device over the secure communication pathway. In some cases, data indicating an instruction to the implantable device can be transmitted from the authorized device over the secure communication pathway. For example, data instructing the implantable device to deactivate itself can be received from the authorized device over the secure communication pathway.

According to particular implementations, the authorized device can be another implantable device. In some cases, a group of implantable devices can establish secure communication pathway(s) between each other and can exchange data with each other via the secure communication pathway(s). In some cases, the group of implantable devices can exchange data indicating condition(s) of an individual (e.g., a heart rhythm, an insulin level, a blood pressure, any other condition sensed by sensor(s) associated with the implantable devices, etc.) over the secure communication pathway(s). In certain implementations, the group of implantable devices can exchange data indicating instructions for performing one or more actions, such that a first implantable device can cause a second implantable device to perform an action by instructing the second implantable device to perform the action. Accordingly, the group of implantable devices can coordinate with each other. In some cases, a "queen" implantable device can receive data packets indicating sensed conditions of an individual (e.g., a heart rhythm, an insulin level, a blood pressure, etc.) from one or more "worker" implantable devices and can transmit data packets indicating instructions to perform actions based on the sensed conditions to the one or more worker implantable devices.

In particular examples, a pacemaker device, upon sensing a heart arrhythmia in an individual, may transmit, to a neural implant device associated with the individual, an instruction to at least temporarily deactivate by electrically disconnecting from a neuron of the individual. When the neural implant device is deactivated, the pacemaker device can electrically stimulate a heart of the individual. This may prevent the neural implant device from being damaged by the electrical stimulation performed by the pacemaker device. In some cases in which the neural implant device includes an electrical sensor, the deactivation of the neural implant device can prevent the neural implant device from sensing and mistaking an electrical current associated with the pacemaker as a trigger to perform an unnecessary action (e.g., electrical stimulation) on the neuron.

The disclosed systems and methods provide various technical advantages. One advantage is a network of devices collectively providing real-time data about organs to a monitoring station. Another advantage is a network-based control system that ensures electronic security and data integrity for data associated with the implantable devices. Another advantage is storing local data in secure locations or databases within artificial devices. Another advantage is implantable systems may execute in a secure fashion to enhance cybersecurity.

The techniques and systems described herein may be implemented in a number of ways. Example implementations are provided below with reference to the following figures.

FIG. 1 is a schematic diagram of an illustrative environment 100 for securing devices implanted subcutaneously in a body, including in human organ systems. Environment 100 depicts implantable devices implanted subcutaneously in a person 101. FIG. 1 depicts an implantable device 102 monitoring the heart, implantable glucose monitoring device 104, implantable retinal device 106 facilitating vision, cochlear implant 108 facilitating aural senses, implantable memory chip 110 facilitating memory recall, implantable device 112 responding to an adverse cardiac event, artificial wrist or artificial elbow 114, artificial mechanical knee joint 116, and implantable gateway 120. Of course, any number and/or type of implantable devices can be implanted or operated in connection with a person. Further, although discussed in the context of implantable devices, the techniques and systems discussed herein apply to devices that are partially or wholly implanted in a body of a person. In other example, the techniques and systems discussed herein apply to devices that are external to a body of a person.

One example heart monitoring device 102 is an artificial heart device (e.g., a pacemaker) that facilitates pumping blood throughout the body as shown in FIG. 1. In this example, the implantable device 102 includes a secure boot component 150, an operational component 152, a maintenance component 154, a deactivation component 156, and a key database component 158. Each implantable device 102, 104, 106, 108, 110, 112, 114, 116, 120 shown in FIG. 1 may include the secure boot component 150, the operational component 152, the maintenance component 154, the deactivation component 156, and the key database component 158.

The secure boot component 150 may initiate operation of the implantable device. When inserted in a body, the implantable device may perform a self-check routine as part of the boot process to initiate the operation of the device. During this secure boot component, errors or other abnormal conditions of the implantable device may be identified. The secure boot component may also boot the operating system of the implantable device for facilitating software control of the implantable device hardware.

The secure boot component 150 for an implantable device may provide power to the implantable device, obtain a key unique to the implantable device, confirm the key unique to the implantable device, boot the implantable device, establish a secure communication pathway, and communicate securing over the secure communication pathway. A key may be unique to an authorized user or to an implantable device. The implantable device may maintain a database or list of acceptable or authorized keys. In another example, information regarding the authorized unique keys may be stored on a device separate from the implantable device and may be accessible by the implantable device. During the secure boot process, the key can be compared to the acceptable or authorized keys as a gating function to completion of the secure boot process. Confirmation of the unique key of the implantable device may facilitate the security of the boot process. In one example, the controller of the implantable device confirms whether the unique key is authorized, and if authorized, the secure boot process may be executed. The operations associated with the key, including retrieval, comparison, and analysis, are performed by the key database component 158.

The operational component 152 can control normal and expected operation of the implantable device. For example, normal operation for a pacemaker may include, for example, electrical pacing of the heart, when necessary, and recording the heart rhythm, whereas normal operation of an implantable cardioverter defibrillator may include the operational steps of a pacemaker combined with monitoring and converting a patient's heart rhythm from abnormal to normal.

The maintenance component 154 can be configured to ensure proper and accurate operation of the implantable device during normal operation. Functions performed by the maintenance component 154 may include self-diagnostic operations of the implantable device, the installation of software updates or upgrades, and software to resolve errors or potential errors in the implantable device. For example, a memory optimization routine may be included in the maintenance component 154 to ensure the efficient use of memory, including removing bad memory blocks and optimizing memory storage.

An implantable device may be decommissioned or deactivated by a deactivation component 156. For example, it may be necessary to deactivate an implantable device when a patient is undergoing surgery or another medical procedure that may be compromised by the implantable device. A medical provider may be given access to information about deactivating an implantable device, even if the patient has not previously seen the medical provider. In another example, an implantable device may be deactivated upon determining that the implantable device's operation is harming or not otherwise helping the patient and should be removed from service. An implantable device may be deactivated by removing it from the body, inactivating it, or supplanting it by another device.

Another heart monitoring device 102 is a pacemaker optionally combined with a defibrillator or an implantable cardioverter defibrillator. The heart monitoring device 102 may be configured to identify aberrant heart rhythms and respond accordingly. For example, if the implantable device determines that the heart experience an aberrant heart rhythm such as sinus tachycardia, the defibrillator of implantable device 102 may discharge to convert the tachycardia into a normal rhythm to reestablish a normal heart rhythm.

Implantable devices may also include a glucose monitoring device 104 for continuous monitoring of glucose levels or injection of insulin via an insulin pump. The insulin pump may inject insulin at specific times or in response to monitoring blood glucose levels to maintain normal glucose levels. Another example of an implantable device for glucose regulation is an artificial pancreas. In another example, an insulin pump may be combined with an artificial pancreas for real time glucose monitoring.

One example implantable retinal device 106 is a retinal prosthesis or a retinal chip implant. Retinal implants may stimulate surviving retinal neurons to produce visual information into the retina, allowing some people to regain some vision. Another implantable retinal device may capture and convert visual images into electrical pulses that are wirelessly communicated to electrodes that stimulate the visual cortex, restoring vision in some people.

One example aural implant 108 is a cochlear implant. Cochlear implants bypass damaged ear structures and may directly stimulate the auditory nerve. These devices may improve hearing in people with severe hearing loss. Further, a brain implant 110 may be implanted in a brain. The brain implant 110 can include one or more memory chips that can be configured to enhance memory recall, eliminate memories, and treat dementia-related diseases such as Alzheimer's disease. Other implantable devices include artificial hands 114 and knees 116. Prosthetic devices have greatly enhanced the life of amputees or individuals otherwise missing limbs. Artificial elbows, wrists, and artificial knees permit amputees to function almost as they did before their amputations.

In some instances, an implantable device can include a nitroglycerin patch 112. In some instances, nitroglycerin may be important in responding to angina symptoms such as chest pain or pressure before or during an adverse cardiac event such as a heart attack. Introducing nitroglycerin into the body dilates blood vessels to increase the blood flow to the heart, potentially minimizing the damage resulting from an adverse cardiac event. It is expected that the nitroglycerin patch 112 may be implanted in the body and controlled by a monitoring device. The inclusion of a nitroglycerin component would reduce or minimize the time the body is in distress.

In addition to implanted in a body, environment 100 may also include gateway 120 to manage the flow of data through communication pathways. The gateway 120 may control data flow between implantable devices in environment 100, as well as control data flow between environment 100 and external devices. Implanting gateway 120 in a body can provide a single source of contact with external devices. Moreover, gateway 120 may also serve as a firewall or proxy server to minimize unauthorized intrusions into environment 120.

Further, the environment 100 can include a gateway 120. The gateway 120 can be implemented as a node for providing a communication pathway with the implantable devices shown in FIG. 1. The implantable devices shown in FIG. 1 may be wirelessly connected to the gateway 120. The wireless connection is a communication pathway to transmit information to or from the implantable devices. In this example, external devices may establish a communication pathway with gateway 120 to communicate with implantable devices shown in FIG. 1. In one example, managing the secure communication pathways manifested by wireless communications through gateway 120 facilitates secure communication with external devices.

Figure 2:
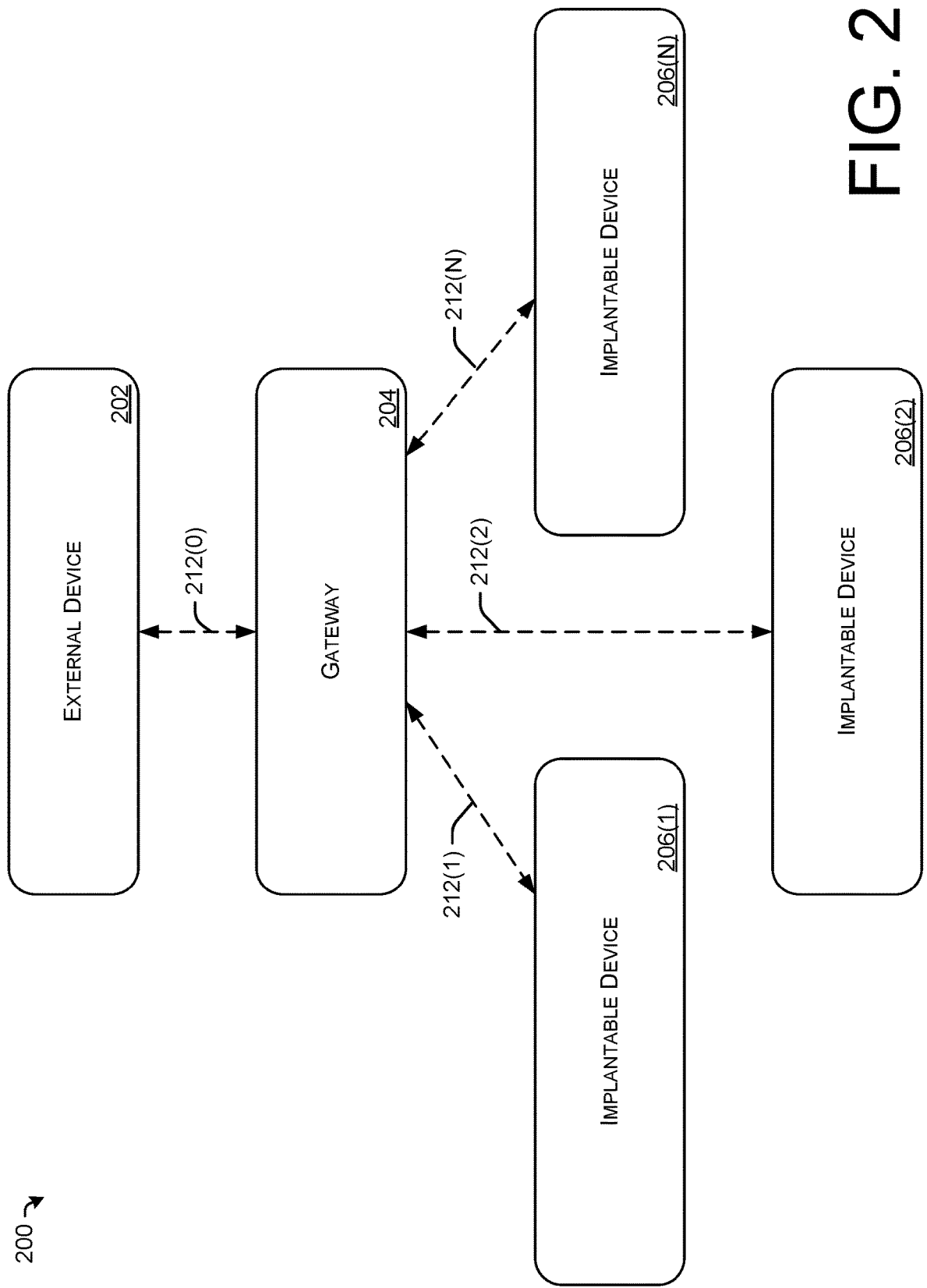
FIG. 2 illustrates an example communication topology including implantable devices.

FIG. 2 illustrates an example communication pathway topology 200. The topology in FIG. 2 can include an external device 202, a gateway 204, an implantable device 206(1), an implantable device 206(2), and an implantable device 206(N). FIG. 2 illustrates wireless communication channels 212(1), 212(2), and 212(N) coupling these devices to the gateway 204, and wireless channel 212(0) coupling the gateway 204 to the external device 202. It is understood that wireless communication channels 212(0), 212(1), 212(2), and 212(N) may be implemented as one wireless channel or multiple wireless channels. In one example, implantable devices 206(1), 206(2), and 206(N), and external device 202 each register with gateway 204. In this example, a portion or all communication between external device 202 and implantable devices 206(1), 206(2), and 206(N) proceed through gateway 204. Gateway 204 can be a node through which all communication may travel. In another example, some or all implantable devices 206(1), 206(2), and 206(N) may communicate directly without sending communication data through gateway 204.

Using the gateway 204 as a node through which external communications travel may enhance security and operation of the system. In one example, external devices need only by aware of the communication pathway and protocol associated with communicating with the gateway 204. By doing so, in one example, the implantable devices may be undetectable by external devices. Additionally, only the gateway 204 need be aware of the communication protocols, communication pathways, and implantable devices within a body. Barring external devices from knowledge or awareness of communication protocols and pathways associated with implantable devices may enhance the security of data related to implantable devices and allow proprietary protocols to be designed into implantable devices. Furthermore, because the implantable devices such as 206(1), 206(2), and 206(N) may remain close to other devices implanted in a body, an arrangement using a gateway may allow transmission of lower signal strength messages, which may prolong the life of the power source of the implantable device.

Figure 3:
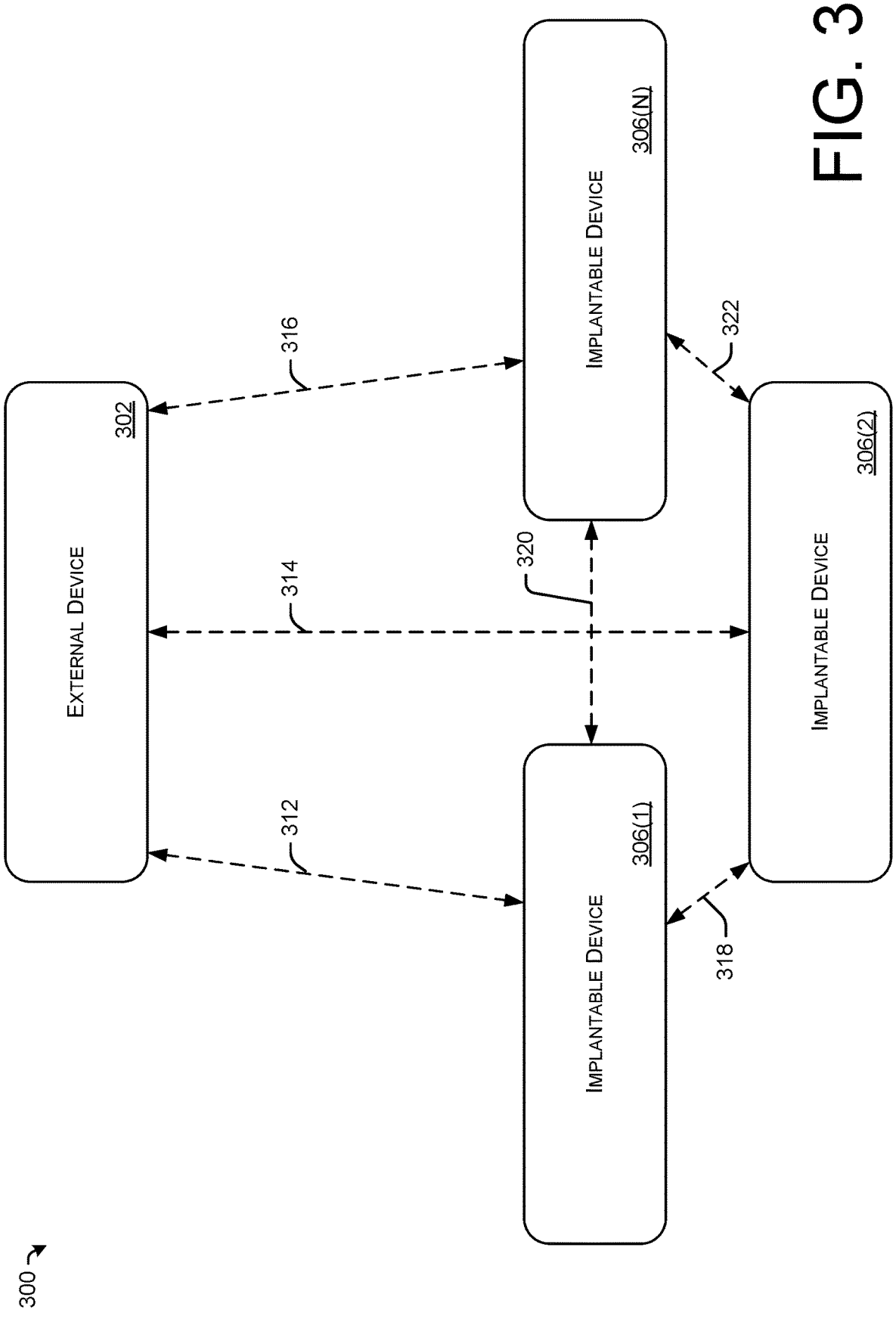
FIG. 3 illustrates an example communication topology including implantable devices.

FIG. 3 illustrates an example communication pathway topology 300. The communication pathways in FIG. 3 between external device 302 and implantable devices 306(1), 306(2), and 306(N) are linked by wireless communication channels 312, 314, and 316, respectively. Communication channel 318 links implantable devices 306(1) and 306(2). Communication channel 322 links implantable devices 306(2) and 306(N). Communication channel 320 can facilitate communications by and between the implantable devices 306(1) and 306(N). Because the system illustrated in FIG. 3 may be implemented without a gateway, each device in FIG. 3 can establish a communication channel with another device in the system.

The example systems shown in FIGS. 2 and 3 may inadvertently various entry points for malicious activities to corrupt the system. For example, malicious code may be introduced into implantable devices through the communication pathways (e.g., 212(0), 212(1), 212(2), 212(N), 312, 314, 316, 318, 320, and 322), through the implantable (e.g., 206(1), 206(2), 206(N), 306(1), 306(2), and 306(N)) or external (e.g., 202 and 302) devices, or through the gateway 204. In addition, a malicious actor may gain access to an implantable device through one or more of the communication pathways or devices, potentially causing detrimental effects on the devices and the patient.

Protecting implantable devices against improper use and improper operation may be important for patient health. For example, a malicious actor may hack one implantable device, and in turn may control or hack other implantable devices in the system. The integrity and accuracy of the data associated with an implantable device should be maintained. Establishing secure operation of these devices is a consideration for proper operation. Additionally, unauthorized access of digital data in these implantable devices may raise data privacy issues. The systems and methods of this disclosure may prevent third party intrusions into the system and encrypt the data of these systems to reduce the risk of a privacy breach.

In one example, an implantable device includes a control component for controlling the operation of the implantable device and ensuring secure communication. The control component may be coupled to the implantable device, may be part of a device external to the implantable device, or may be included partially within and partially outside the implantable device. The control component may access data inputs to, and outputs from, an implantable device. The control component performs various functions for secure operation, including a secure boot of the implantable device and establishing secure communication channels with the implantable devices. The control component may also monitor the operation and maintenance of an implantable device, such as battery charge level to determine when to charge or replace the battery of the device.

Figure 4:
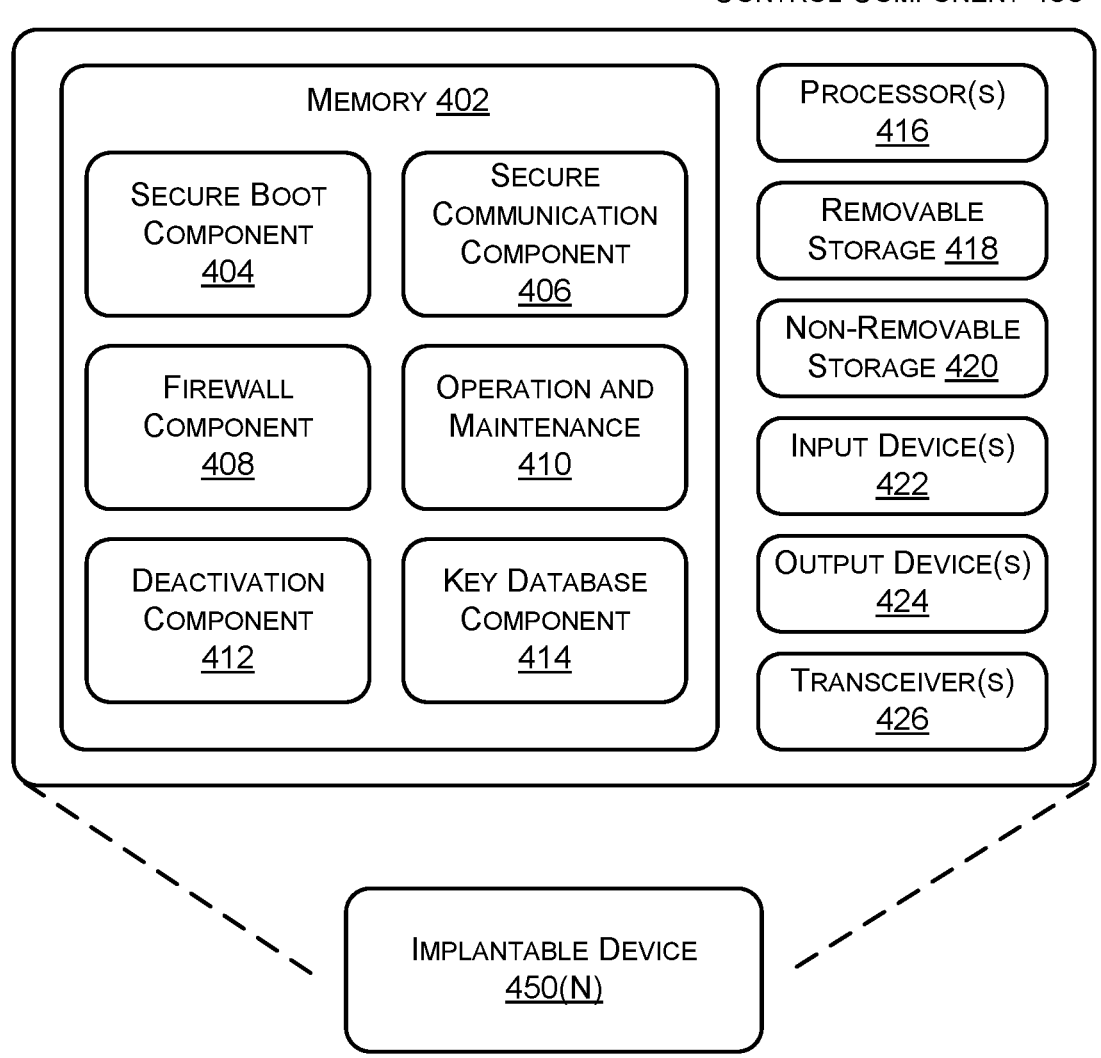
FIG. 4 illustrates an example architecture of a control component associated with an implantable device.

Implantable devices may include a control component to facilitate communication between devices. One example control component for an implantable device 450(N) is shown in FIG. 4. In some implementations, the control component 400 includes a software component stored in memory 402 of implantable device 450(N). Implantable device 450(N) may be any device to be implanted subcutaneously in a body, including those implantable devices shown in FIG. 1. The implantable device 450(N) may be biocompatible. It is understood that the control component 400 may be implemented using software, hardware, firmware, and combinations thereof. The control component depicted in FIG. 4 includes a secure boot component 402, a secure communication component 406, a firewall component 408, an operation and maintenance component 410, a deactivation component 412, and a key database component 414.

The secure boot component 404 ensures the that the associated implantable device boots up properly under the proper authorization. In some examples, the secure boot component 404 can use an authentication key to confirm that the boot function is performed in response to an authorized party or an authorized command. The secure boot component 404 provides performs two separate functions. First, it confirms that the hardware for both the control component and the implantable device has not been modified. In one example, the secure boot component 404 checks a registry entry to determine if the hardware has been modified. The secure boot component 404 may also check hardware capabilities of the implantable device to determine whether the hardware has been modified. Additionally, the secure boot component 404 confirms that the software for both the control component and the implantable device has not been modified. For example, the secure boot component 404 may check a registry file or other file to identify if software has been modified.

Control component 400 may also include a secure communication pathway component 406. Secure communication component 406 can be implemented to ensure that data communication to and from the device is secure. Secure communication component 406 may include at least two aspects: secure data communication and secure access to the communication pathway. One example of secure data communication is the exchange of encrypted data. Along with the encrypted data, a key is received by an authorized device. Using the authorization key, the recipient device decrypts the data and performs its normal processing activities. For secure access to the communication pathway, a key may be required so that only authorized keys can unlock access to secure data communication.

To determine whether a key is authorized, control component 404 may query a key database component 414. In one example, the key database component 414 includes a database of keys. In an example, the key database component 414 queries or otherwise obtains information from an external database. In another example, the key database component 414 may query its database and an external database to determine whether a key is authorized. If the key database component 414 includes an identical key to the unique key, the key is authorized and secure communication occurs. In one example, the unique key for data encryption is used for access to secure communication.

In another example, the unique key for data encryption differs from that for access to secure communication. In this case, two separate keys may be used. A key to decrypt the data and a key allowing for secure communication can be different.

The control component 400 may include an operation and maintenance component 410. In one example, operation and maintenance component 410 monitors operation of the implantable device to identify deviations from the expected normal operation. The operational process of operation and maintenance component 410 ensures that the associated implantable device is operating properly and under normal operations. The control component performs functions during the normal course of operation of the associated implantable device. Operation and maintenance component 410 may identify conditions requiring repairs or input. In one example, operation and maintenance component 4109 may determine when the implantable device needs periodic or emergent repairs. For example, operation and maintenance component 410 may monitor the battery life, and transmit a message indicating that the battery may need replaced. The operation and maintenance component 410 may also monitor the output of the implantable device to identify any monitored parameters are outside the expected or normal range. Upon detecting any out-of-range parameters, operation and maintenance component may send a message identifying that the implantable device is not operating correctly, and further attempting to repair the device, if possible, by performing maintenance on the implantable device to cause it to function properly.

The control component may also include a deactivation component 412. Deactivation component 412 may be run when the implantable device is at its end of life expectancy and is expected to be replaced to turned off. Deactivation component 412 may be run in response to repairing an implantable device during the lifetime operation of the implantable device.

The control component may also include a firewall component 408. The firewall component 408 may serve as a barrier between the implantable device (or network of implantable devices) and the external environment. The firewall component 408 is designed to prevent unauthorized access to and from the implantable device. The firewall component may be implanted in hardware, software, or a combination of hardware and software.

In some embodiments, the control component includes processor(s) 416. Processor(s) 416 may be any type of processing, including a central processing unit (CPU), a graphics processing unit (GPU), or both CPU and GPU, or other processing unit or component known in the art.

The control component 400 may also include additional data storage devices (removable and/or non-removable) such as, for example, magnetic disks, optical disks, or tape. Such additional storage is illustrated in FIG. 4 by removable storage 418 and non-removable storage 420. Tangible computer-readable media can include volatile and nonvolatile, removable and non-removable media implemented in any method or technology for storage of information, such as computer readable instructions, data structures, program modules, or other data. Memory 402, removable storage 418 and non-removable storage 420 are examples of computer-readable storage media. Computer-readable storage media include, but are not limited to, RAM, ROM, EEPROM, flash memory or other memory technology, CD-ROM, digital versatile discs (DVD), content-addressable memory (CAM), or other optical storage, magnetic cassettes, magnetic tape, magnetic disk storage or other magnetic storage devices, or any other medium which can be used to store the desired information and which can be accessed by the control component 400. Any such tangible computer-readable media can be part of the user control component 400.

Control component 400 can include input device(s) 422, such as a keypad, a cursor control, a touch-sensitive display, voice input device, etc., and output device(s) 424 such as a display, speakers, printers, etc. In some instances, the input device(s) 422 can include at least one sensor, such as at least one a temperature sensor, a pH sensor, an electrical sensor, a pressure sensor, a microphone, a movement sensor, a chemical sensor, or the like. In particular implementations, the output device(s) 424 can include a pacemaker circuit configured to deliver an electric shock to the heart of a patient, a cochlear implant circuit configured to stimulate an auditory nerve of a patient, an insulin pump configured to inject an amount of insulin into a bloodstream of a patient, a prosthetic device configured to move a prosthetic limb, a retina implant circuit configured to stimulate a retina of a patient, a neural implant circuit configured to electrically stimulate a nerve of a patient, a brain implant circuit configured to electrically stimulate a portion of a brain of a patient, and the like.

The input device(s) 422 may be configured to sense a condition, monitor the condition, and cause the output device(s) 424 to take certain actions based at least in part on the condition. For instance, when an electrical sensor of the input device(s) 422 senses an irregular heart rhythm, the processor(s) 416 may control a pacemaker circuit of the output device(s) 424 to electrically stimulate the heart of the patient. In some examples in which a chemical sensor of the input device(s) 422 sense an insulin level in a blood sample outside of a particular range, the processor(s) 416 may control an insulin pump of the output device(s) 424 to inject an amount of insulin into a bloodstream of the patient.

As illustrated in FIG. 4, the control component 400 also includes one or more wired or wireless transceiver(s) 426.

For example, the transceiver(s) 426 can include a network interface card (NIC), a network adapter, a LAN adapter, or a physical, virtual, or logical address to connect to various network(s), or to the control component 400, for example. To increase throughput for exchanging wireless data, the transceiver(s) 426 may utilize multiple-input/multiple-output (MIMO) technology or other high throughput wireless standards such as 802.11ac. The transceiver(s) 426 may comprise any type of wireless transceivers capable of engaging in wireless, radio frequency (RF) communication. The transceivers 426 can also include other wireless modems, such as a modem for engaging in Wi-Fi, WiMax, Bluetooth, or infrared communication.

The wireless transceiver 414 may wirelessly receive and transmit data. The wireless transceiver 414 may be included in a wireless communication chip. The wireless communication chip in one example may be located in the control component 400. In another example, the wireless communication chip may be located on a separate wireless component. The control component 400 may also include a firewall component 408. Firewall component 408 may be responsible for all protocols required for data transmission to and from the device.

In one example, a secure communication pathway may be a wireless channel. For example, each device may have a wireless transmitter and receiver compliant with a wireless protocol. Example wireless protocols include Wi-Fi (including 802.11-based technologies), cellular data service (including GSM, CDMA, CPRS, 4G, W-CDWM, EDGE, CDMA2000, LTE), WiMAX, Bluetooth, Zigbee (802.15.4-based technologies), near field communication, frequency hopping, and the like.

In one example, the control component 400 may be designed to integrate with one implantable device. In this case, the hardware, firmware, and software of the control component 400 may be tailored to operate as a control component 400 for one specific implantable device. In another example, the control component 400 may be a universal control component configurable to function as a controller for different implantable devices. For example, a universal control component may be configured as a control component for a pacemaker, for an artificial pancreas, or for an implantable retina, among others. In another example, like a general computer processor, a universal control 400 component may be software configurable to perform specific functions, depending on the implantable device it is coupled to.

In another example, the control component 400 may be wirelessly coupled to each implantable device. This allows the control component 400 to control multiple implantable devices simultaneously. A single universal control component 400 may also simplify the design and operation of the implantable devices because only a single control component need be designed and operated. This single control component 400 may be easier to debug and design, leading to a more efficient and accurate implantable device system.

In another example, the control component 400 may be a generic software component executing software to perform network virtualization. These generic control components may be applied to any organ systems. In one example, the generic control component may be programmed to operate as a heart. In other example, the generic control component may be programmed to operate as a liver. The functionality of the generic control components may vary based on software, rather than hardware. Once connected to an implantable device, the generic control component communicates securely, either via a gateway hub or via a direct connection with other implantable devices as discussed herein.

Figure 5:
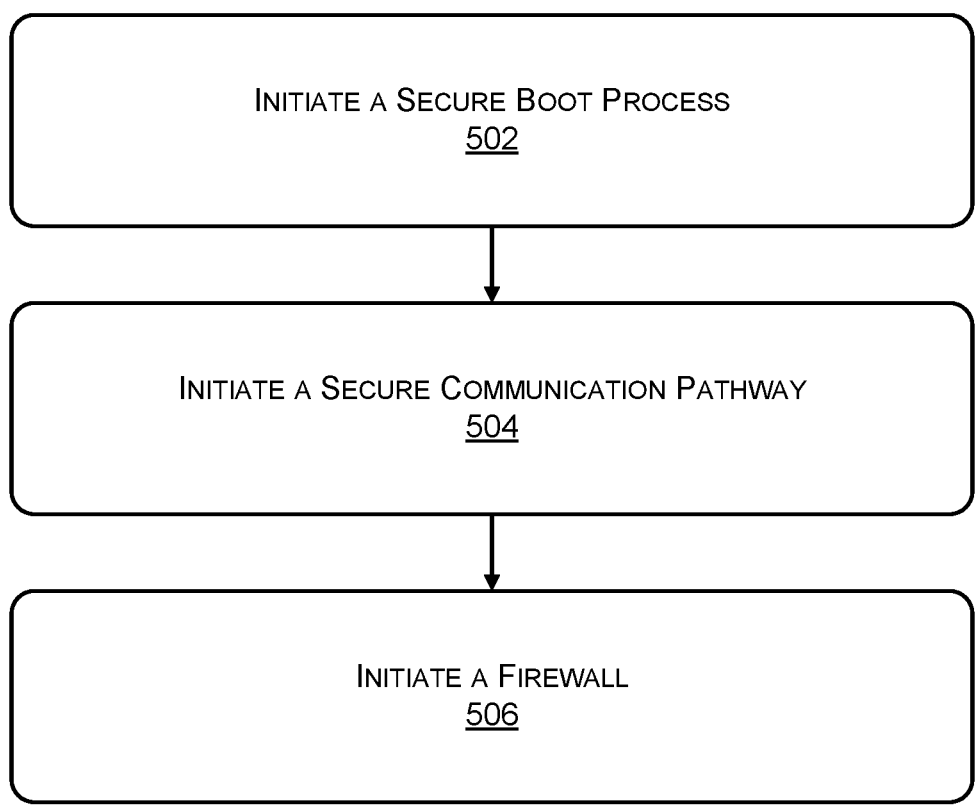
FIG. 5 illustrates example steps or functions performed by the control component.

One example of a flow chart of the functions or steps performed by the control component is shown in FIG. 5. In this case, the control component performs three functions shown in process 500: a built-in boot process 502, a secure communication 504, and a firewall 506. Before operation, the electronics in the implantable device may be securely started up through a boot process. A secure boot process 502 is initiated to ensure that the implantable device is properly controlled during start up to reduce the risk that a rogue actor or unauthorized third party may control the implantable device. A secure boot process initiates secure communication before the implantable device communicates with the environment or external devices. The secure boot process 502 confirms the integrity of the hardware and software of the communication component 400. The secure boot process may be updated during the life of the implantable device.

After the implantable device is initialized through a boot process, the implantable device initiates a state of secure communication operation 504. The secure communication pathway 504 maintains data integrity and reduces the risk of eavesdropping or collecting data by an unauthorized source. One method of secure communication pathway applies an encryption process to the data. The encryption process may be controlled by an authorization key passed from another device. If the authorization key matches the key used during encryption, the data may be decrypted by the recipient for further use. In another example, the encrypted data may be sent with a key that may be accessed only by an authorized device. If authorized, the device may decrypt the received encrypted data. By permitting only authorized devices or people to communicate with the implantable device, the secure key may prevent malicious operation of the implantable device.

The secure communication pathway function 504 may include a handshaking protocol utilizing a key to enable or unlock the communication. When attempting to access or communicate with the implantable device, a requesting device may send a key to the implantable device. If the key matches an authorized key, the implantable device may allow the requesting device to communicate with the implantable device. This approach reduces the risk that an authorized device may maliciously communicate with the implantable device. Similarly, secure communication between implantable devices minimizes or reduces the risk that the implantable device may communicate with an unauthorized device. Secure communication minimizes the malicious use of implantable devices.

In some examples, the secure key may be derived from an individual (e.g., the patient). For example, the secure key may be based on genetic information of an individual. The secure key may be based on underlying brainwaves or heart rhythms of the individual. In other cases, the secure key may be based on a person's gait, or other features such as facial structure, teeth structure, or other features unique to an individual.

In an example, secure communication 504 occurs between an implantable device and the gateway, if present. In an example, the secure communication channel operates between implantable devices implanted in a body. In an example, the secure communication channel operates between implantable devices and devices located outside the medium containing the implantable device.

The control component may initiate and perform a firewall function 506. The firewall 506 can be a barrier between the implantable device and external devices for secure communication with the implantable device. The firewall can monitor and control incoming and outgoing communication traffic to the implantable device or gateway. The firewall can operate using security rules that may be different from those of the secure communication function 504. The firewall 506 may operate using security rules that are coextensive with those of the secure communication function 504. The secure communication function and the firewall 506, separately or in combination, reduces the risk that a rogue actor may gain control of the implantable devices.

Figure 6:
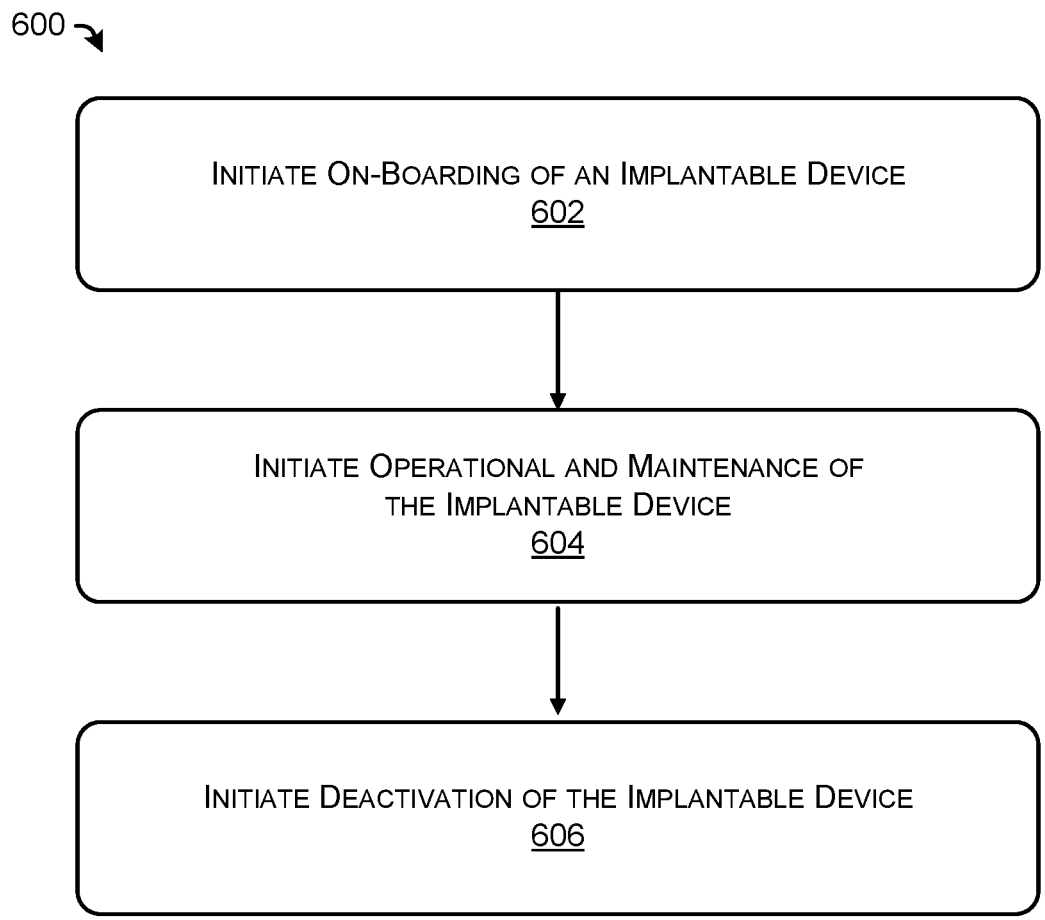
FIG. 6 illustrates an example process for a life cycle of an implantable device.

An implantable device may initiate and operate different functions throughout the life cycle of an implantable device. One example life cycle process 600 is shown in FIG. 6. One or more of the functions performed during the life cycle stages may be controlled by the controller. The first phase of the life cycle is the on-boarding 602 of the implantable device. The on-boarding 602 of the implantable device may implanting the device in the body. The on-boarding 602 may also include a secure boot process for initializing the implantable device. The secure boot process may ensure that the implantable device is properly turned on and initialized and its functions are under the proper control.

After the implantable device is on-boarded and/or initialized, the device enters an operational phase 604. During the operational phase 604, the implantable device operates ensuring that the implantable device functions correctly and communicates securely. In an example, the secure communication is controlled by the controller. During the operation phase 604, the implantable device may execute diagnostic tests and software to confirm that the implantable device is operating properly, and to identify if the implantable device requires maintenance for proper operation. These diagnostic tests and software may be stored in and executed by the controller. As maintenance issues are identified, the implantable device may require a hardware or software patch to fix the identified problems. In another example, the software of the implantable device may require an upgrade to resolve issues or to add to or subtract from functionality from the implantable device. The controller may be responsible for installing the upgrade.

The third phase of the life cycle of an implantable device may be the deactivation or decommission 606 of the implantable device. During deactivation, the operation of the implantable device is turned off in response to various scenarios. In an example, the implantable device may be no longer needed and therefore may be shut down or decommissioned. In an example, the operation of the implantable device may be counterproductive and cause harm to the patient, requiring the device to be shut down or decommissioned. As an optional part of the deactivation process 606, the deactivated implantable device may be replaced with a separate implantable device. Upon replacement, the original, deactivated implantable device may be removed. In another example, the original, deactivated implantable device may remain in the body.

The life cycle of the implantable device may be controlled by a management process. The management process may be included in the control component or in the gateway. One function of a management process is deactivating an implantable device. In one example, a management process may decommission an implantable kidney following an introduction of a replacement implantable kidney. Following initiation of the implantable device, the management process starts the decommission process. Additional management functions include inactivating or causing an implantable device to become dormant or nonfunctional. The management process may also control the operation and maintenance monitoring of the implantable device.

Figure 7:
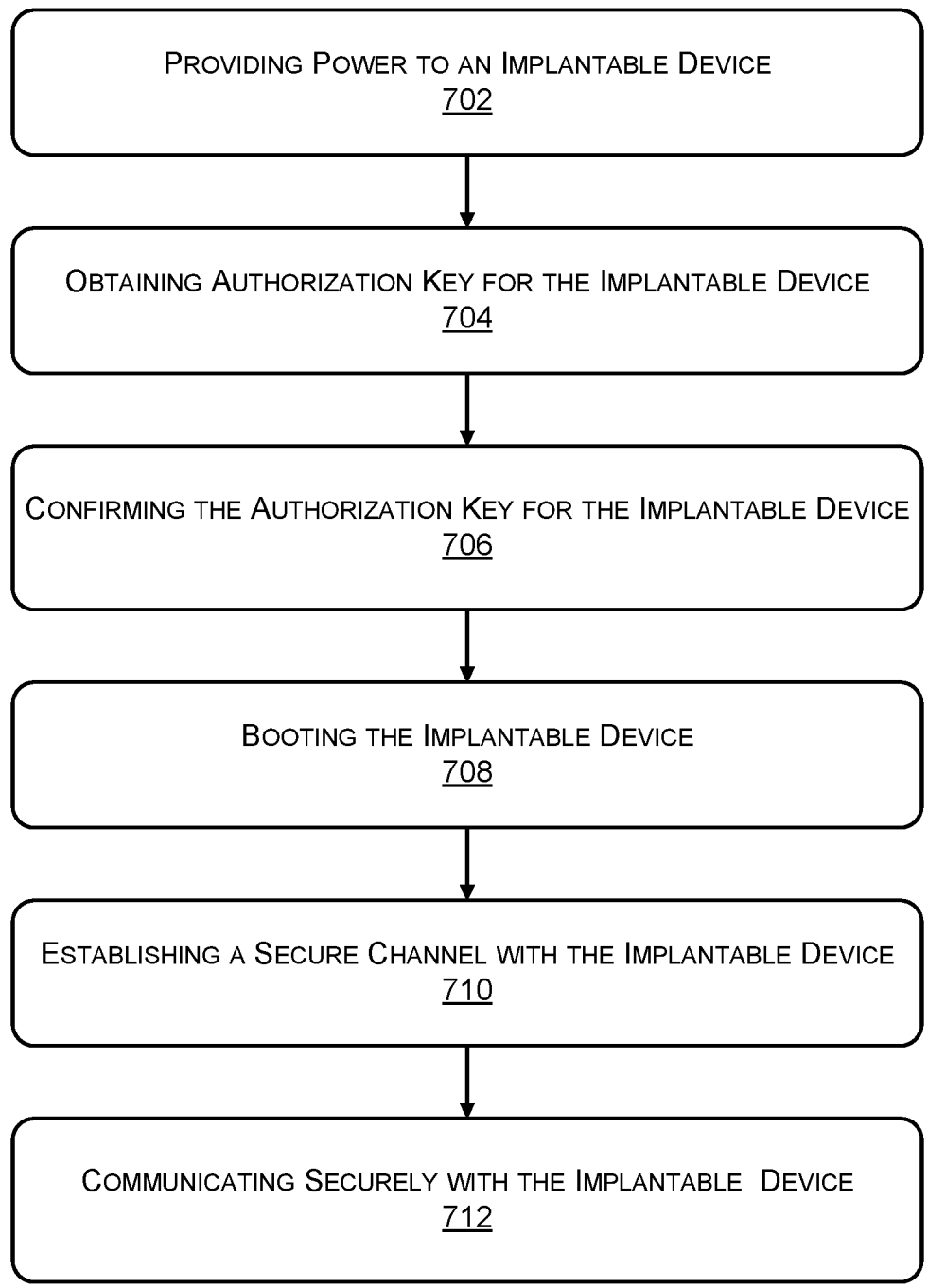
FIG. 7 illustrates an example boot process for an implantable device.

One example secure boot process for an implantable device is illustrated in FIG. 7. The secure boot process begins with applying power to the implantable device at operation 702. In one example, the power may come from a battery. In an example, the power may come from an inductive coil exchanging power to the implantable device.

After application of power, the secure boot process may continue at operation 704. Initiation of the boot process occurs when the controller of the implantable device receives an authorization key. In some cases, the authorization key can be received from a separate device. An authorization key adds an extra layer of security so that the secure boot process is performed in response to an authorized request. After receiving an authorization key, the controller confirms the identity of the authorization key at operation 706 before proceeding. In an example, the implantable device controller compares the received authorization key to those stored in a database. In an example, the implantable device controller may compare the authorization key against other keys stored in a database under its control, under the control a third-party database, or under joint control with a third party. Upon confirmation of the authorization key, the implantable device may continue with the boot process.

Once the authorization key has been confirmed, the boot process may be executed on the implantable device at operation 708. During boot process 708, the implantable device executes processes to ensure that the implantable device operates properly. The secure boot process ensures that the boot process is performed after a boot key has been confirmed as authorized and not controlled by a rogue or unauthorized actor. The secure boot process may also confirm that neither the hardware nor the software of the implantable device or control component has been modified.

Following (or as part of) the boot process, the controller establishes a secure communication channel with the implantable device at block 710. In one example, the secure channel uses a handshaking protocol that exchanges an authorization key for security. In one example, the authorization key for the boot process may also function as the authorization key for establishing the secure communication channel. In an example, the authorization key may be unique from the boot authorization key, thereby adding an extra layer of security to the boot process shown in FIG. 7.

Various secure channels may be established during secure channel setup 710. In one example, secure channels may be established between the implantable device and a gateway. The gateway functions as a node between the implantable device and other devices. An example gateway is illustrated in FIG. 1. The other devices may be devices outside the body or inside the body. A gateway provides a node through which communications may be routed. This single node approach may facilitate communications with the implantable device as all communications go through the gateway. In another example, a secure communication channel is established between the implantable device and any other device for communication. These devices may be located inside the body or may be external devices. In this example, each implantable device may set up a secure communication pathway to other authorized devices to minimize the risk of unauthorized devices accessing the secured communication pathway. In one example, the communication channel is a wireless channel.

At operation 712, after the communication channel is established, the implantable devices may communicate securely with each other. Secure communication may occur between implantable devices or between an implantable device and a device located outside the body.

The disclosed systems and methods can provide an enhanced layer of security aimed toward preventing malicious operation or hacking of implantable devices. This enhanced layer of security may be provided by a component that allows secure communications to and from implantable devices. The disclosed systems also permit peer-to-peer communication between implantable devices. The disclosed systems permit implantable devices to be wirelessly connected to networks or hotspots enabling control of implantable devices and analysis of data by external devices. Such devices can be used to control hormone levels through remote monitoring.

The communication pathway is not limited to wireless technologies. For example, a communication pathway within a body may be based on intrabody communication (IBC). IBC uses the human body as a propagation medium. The disclosed systems and methods may be applied to IBC communication between implantable devices and between implantable and external devices.

Although embodiments have been described in language specific to structural features and/or methodological acts, it is to be understood that the disclosure is not necessarily limited to the specific features or acts described. Rather, the specific features and acts are disclosed as illustrative forms of implementing the embodiments.

What is claimed is:

1. A system comprising:
a first implantable device configured to be implanted subcutaneously in a body;
a second implantable device configured to be implanted subcutaneously in the body; and
a control component coupled to the first implantable device, the control component including a processor having computer instructions that when executed cause the processor to perform operations comprising:
establishing a secure boot process of the first implantable device implanted subcutaneously in the body;
wherein a key is compared to authorized keys as a gating function for completion of the secure boot process, wherein confirmation of the key unique to the first implantable device facilitates the security of the secure boot process;
identifying an authorized device;
establishing a first secure communication pathway between the first implantable device and the authorized device;
identifying an unauthorized device;
blocking communications between the first implantable device and the unauthorized device;
establishing a direct peer-to-peer secure communication pathway between the first implantable device and the second implantable device; and
exchanging data between the first implantable device and the second implantable device via the direct peer-to-peer secure communication pathway.

2. The system of claim 1, further comprising:
a firewall component;
an operation and maintenance component;
a deactivation component; and
a key database component.

3. The system of claim 1, wherein the secure boot process of the first implantable device includes:
receiving the key;
determining the key is an authorized key; and
in response to determining the key is an authorized key, booting the first implantable device.

4. The system of claim 1, further comprising a gateway coupled to the first secure communication pathway.

5. The system of claim 1, wherein the first secure communication pathway operates according to a secure communication protocol, the secure communication protocol including a handshaking protocol that utilizes the key.

6. The system of claim 1, wherein the first secure communication pathway includes a secure communication channel between the first implantable device and the authorized device.

7. The system of claim 1, wherein the first secure communication pathway includes a first secure communication channel between a gateway and the first implantable device and a second secure communication channel between the gateway and the authorized device.

8. The system of claim 1, wherein the first implantable device is at least one of a pacemaker, a cardioverter defibrillator, an artificial pancreas, a glucose monitor, an insulin pump, an artificial kidney, a cochlear implant, an artificial joint, an artificial knee, an artificial elbow, a retina implant, or an iris implant.

9. The system of claim 8, wherein the first secure communication pathway is a wireless communication channel compliant with at least one of a 802.11 family of protocols, Bluetooth, Zigbee, LTE, Wi-MAX, Wi-Fi, near field communication, or frequency hopping.

10. A method comprising:
providing power to a first implantable device and a second implantable device, the first implantable device and the second implantable device implanted subcutaneously in a body;
obtaining an authorization key unique to the first implantable device;
confirming the authorization key unique to the first implantable device, wherein the authorization key is compared to authorized keys as a gating function for completion of a secure boot process, wherein confirmation of the authorization key unique to the first implantable device facilitates the security of the secure boot process;
in response to confirming the authorization key:
booting an operating system of the first implantable device, and establishing a first secure communication channel between the first implantable device and a second device;
establishing a direct peer-to-peer secure communication channel between the first implantable device and the second implantable device; and
exchanging data between the first implantable device and the second implantable device via the direct peer-to-peer secure communication channel.

11. The method of claim 10, further comprising communicating between the first implantable device and the second device over the first secure communication channel.

12. The method of claim 10, further comprising:
detecting an abnormal condition of the first implantable device.

13. The method of claim 10, wherein the second device is at least one of a gateway device or an external device.

14. A method for operating a first implantable device performed by a processor of a control component executing computer instruction, the control component coupled to the first implantable device and a second implantable device, the method comprising:

securely booting the first implantable device, the first implantable device configured to be implanted subcutaneously in a body, wherein a key is compared to authorized keys as a gating function for completion of the secure boot process, wherein confirmation of the key unique to the first implantable device facilitates the security of the secure boot process;

identifying an authorized device;

identifying an unauthorized device;

communicating securely between the authorized device and the first implantable device via a first secure communication link, wherein the unauthorized device is prevented from accessing the first secure communication link;

blocking communications between the first implantable device and the unauthorized device;

establishing a direct peer-to-peer secure communication link between the first implantable device and the second implantable device, the second implantable device configured to be implanted subcutaneously in the body; and exchanging data between the first implantable device and the second implantable device via the direct peer-to-peer secure communication link.

15. The method of claim 14, wherein communicating securely with the first implantable device includes operating according to a secure communication protocol, the secure communication protocol including a handshake protocol that utilizes a key.

16. The method of claim 14, wherein the authorized device is a gateway device.

17. The method of claim 14, wherein the first secure communication link includes a first secure communication channel between a gateway and the first implantable device and a second secure communication channel between the gateway and the authorized device.

18. The method of claim 14, wherein the first secure communication link is a wireless communication channel compliant with at least one of 802.11 family of protocols, Bluetooth, Zigbee, LTE, Wi-Fi, near field communication, and frequency hopping.

19. The method of claim 14, further comprising initiating a firewall.

* * * * *